US00PP32769P2

(12) United States Plant Patent
Pierron-Darbonne

(10) Patent No.: US PP32,769 P2
(45) Date of Patent: Jan. 26, 2021

(54) STRAWBERRY PLANT NAMED 'PLARED 15105'

(50) Latin Name: ***Fragaria* x *ananassa* Duchesne ex Rozier**
Varietal Denomination: Plared 15105

(71) Applicant: Plantas de Navarra, S.A. Sociedad Unipersonal, Valtierra (ES)

(72) Inventor: Alexandre Pierron-Darbonne, Pamplona (ES)

(73) Assignee: Plantas de Navarra, S.A. Sociedad Universal, Navarra (ES)

( * ) Notice: Subject to any disclaimer, the term of this patent is extended or adjusted under 35 U.S.C. 154(b) by 0 days.

(21) Appl. No.: 16/873,360

(22) Filed: Mar. 26, 2020

(30) Foreign Application Priority Data

Jul. 9, 2019 (QZ) ..... PBR 2019/1674

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./309
See application file for complete search history.

*Primary Examiner* — Annette H Para

(74) *Attorney, Agent, or Firm* — Knobbe, Martens, Olson & Bear, LLP

(57) ABSTRACT

Described is a new and distinct strawberry variety with varietal denomination 'Plared 15105'. The new variety is characterized by a combination of traits which include, medium vigor plants having a semi-upright growth habit, fully remontant, and producing large-size, conical-shaped and firm fruit. 'Plared 15105' is a self-fertile variety.

16 Drawing Sheets

Botanical classification: *Fragaria* x *ananassa* Duchesne ex Rozier.

Variety denomination: The new variety has the varietal denomination 'Plared 15105'.

CROSS-REFERENCE TO RELATED APPLICATIONS

This application claims the benefit of European Community Plant Variety Office Application No. 2019/1674, for a strawberry variety named 'Plared 15105', filed on Jul. 9, 2019, the entirety of which is incorporated by reference herein.

BACKGROUND

Disclosed herein is a new and distinct strawberry variety (*Fragaria* x *ananassa* Duchesne ex Rozier). The varietal denomination of the new variety is 'Plared 15105'. The new variety was designated by the breeder as breeder number '15.04R.199'. The new variety of strawberry was created in a breeding program by crossing two parents in 2015 in Cartaya (Huelva), Spain (about 7° W, 37° N, 45 feet elevation). The seed parent was an undistributed strawberry variety designated '09-55' (unpatented) and the pollen parent was an undistributed strawberry variety designated '09-25' (unpatented). Each parent was a selection from a breeder's program and has not been commercialized.

The resulting seedling of the new variety was grown and asexually propagated by Alexandre Pierron-Darbonne by runners in Segovia, Spain (3° 59'W., 41° 22'N., 2742 feet elevation) and it was successively propagated by runners, first into a screen-house, and after in the fields. Plants of the new variety were further asexually propagated and extensively tested. In order to establish and bring to health the initial head clones, mother plants that had developed several stolons were subjected to a heat treatment, or thermotherapy, at 36° C.-37° C. for 3 to 4 weeks. After that treatment, apical meristems were cut and developed (1 apical meristem corresponding to 1 rooting plant) in an in vitro culture for 5 to 6 weeks. This propagation and testing demonstrated that the combination of traits disclosed herein which characterize the new variety are fixed and retained true to type through successive generations of asexual reproduction.

The growing period in Cartaya (Huelva), Spain (about 7° W, 37° N, 45 feet elevation), where the observations were made, is between about August 4 and December 31 of each year, with a date of first flowering of September 10, for summer plantings, and between about September 24 and May 20 of the next year with a date of first flowering of October 17 for fall plantings. The location where the observations were made is Cartaya (Huelva), Spain and the observed characteristics are believed to apply to plants grown under similar conditions of soil and climate elsewhere.

COMPARISON TO THE PARENTS

The new variety 'Plared 15105' is distinguished from its seed parent '0955' (unpatented) in that the plant of the seed parent shows an upright growth habit, the shape of the base in the terminal leaflet of the seed parent is acute, the fruit of seed parent shows a narrow band without achenes and the position of calyx attachment on the fruit of the seed parent is level with surface. In contrast, the new variety 'Plared 15105' shows a semi-upright growth habit, the shape of the base in the terminal leaflet is obtuse, the fruit shows a medium width band without achenes and the position of the calyx attachment in the fruit of new variety 'Plared 15105' is raised.

The new variety 'Plared 15105' is distinguished there from its pollen parent '09-25' (unpatented) in that the stipule of the leaf of the pollen parent shows a weak anthocyanin coloration, the fruit of the pollen parent shows a narrow band without achenes and the fruit of the pollen parent shows a medium size cavity. In contrast, the stipule of the leaf of the new variety 'Plared 15105' shows a weak or absent anthocyanin coloration, the fruit shows a medium width band without achenes and a small or absent cavity.

COMPARISON TO CLOSEST VARIETY

The new variety 'Plared 15105' is distinguished by having the inflorescence at same level as the foliage and the flower shows a larger size of the calyx relative to the corolla. The fruit of the new variety has a conical shape, large size, and medium red color. The new variety has a raised position of calyx attachment to the fruit. The fruit is firm and shows a medium red colored flesh. The new variety has a very early time of flowering and ripening. 'Plared 15105' is a fully remontat variety.

The new variety 'Plared 15105' resembles the variety 'San Andreas' (U.S. Plant Pat. No. 19,975) but is distinguished by the following characteristics possessed by 'Plared 15105' which are different, or not possessed by, 'San Andreas'.

The leaf of 'San Andreas' shows an RHS Green group color near 135 B to 135 A on the upper side, whereas the new variety 'Plared 15105' shows an RHS Green group color near 141 B to 141 A on the upper side.

The margin of the terminal leaflet in 'San Andreas' is serrate to crenate, whereas the margin of the terminal leaflet in the new variety 'Plared 15105' is crenate.

The flower of 'San Andreas' shows same size of calyx in relation to corolla, whereas the flower of the new variety 'Plared 15105' has a larger size calyx in relation to corolla.

The fruit size of 'San Andreas' is medium, whereas the fruit size of new variety 'Plared 15105' is large.

The fruit of 'San Andreas' shows a narrow width band without achenes, whereas the fruit of new variety 'Plared 15105' shows a medium width band without achenes.

The position of the calyx attachment in the fruit of 'San Andreas' is level with the fruit, whereas the position of the calyx attachment in the fruit of new variety 'Plared 15105' is raised.

The attitude of the sepals in the fruit of 'San Andreas' is upwards, whereas attitude of the sepal in the fruit of new variety 'Plared 15105' is outwards to upwards.

The time of beginning of flowering in 'San Andreas' is medium (not early and not late), whereas time of beginning of flowering in 'Plared 15105' is very early.

The time of beginning of fruit ripening in 'San Andreas' is early, whereas time of beginning of fruit ripening in 'Plared 15105' is very early.

FIG. 13 shows the differences in the upper side color of the leaf and the terminal leaflet margin shape of 'Plared 15105' (designated 15.04R.199 in the figures) and 'San Andreas'. FIG. 14 shows the differences in the size of the calyx in relation to the corolla of 'Plared 15105' and 'San Andreas'. FIG. 15 show the differences in the fruit size, width of the band without achenes and attitude of the sepals of 'Plared 15105' and 'San Andreas'. FIG. 16 shows the difference in the position of the calyx attachment with the fruit in 'Plared 15105' and 'San Andreas'. These differences are maintained throughout the harvest season.

BRIEF DESCRIPTION OF PHOTOGRAPHS

The accompanying photographs show typical specimens of the new variety, designated 15.04R.199 in the illustrations, including fruit, foliage and flower, in color as nearly true as it is reasonably possible to make in color illustrations of this character.

The plants depicted in the drawings were planted September 24 at the farm of La Mogalla in Cartaya (Huelva), Spain (about 7° W, 37° N, 45 feet elevation).

Photographs were taken March-April (about March 25 and April 25) when there was a minimum temperature of about 10 to 12° C. and a maximum temperature of about 22 to 24° C.

DESCRIPTION OF THE NEW VARIETY

Figure 1:
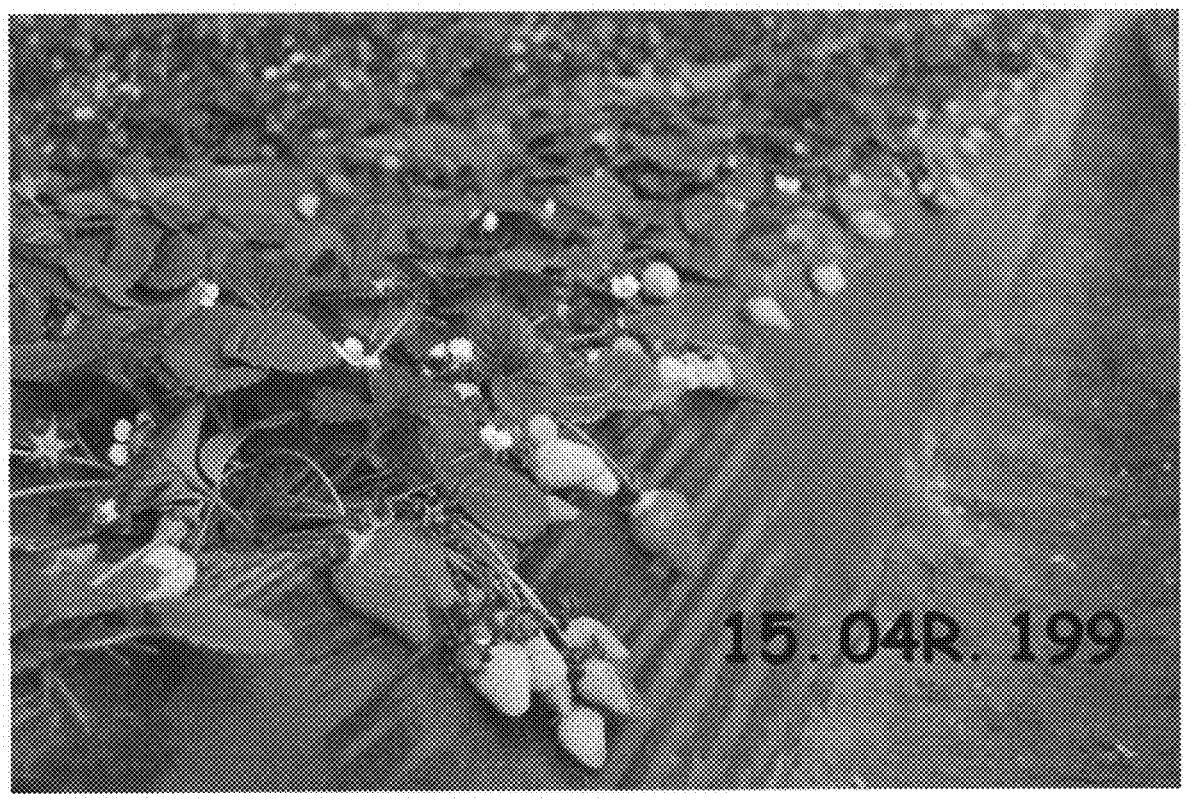
FIG. 1 shows several plants of the new variety having several medium red colored and conical shape fruits.
Figure 2:
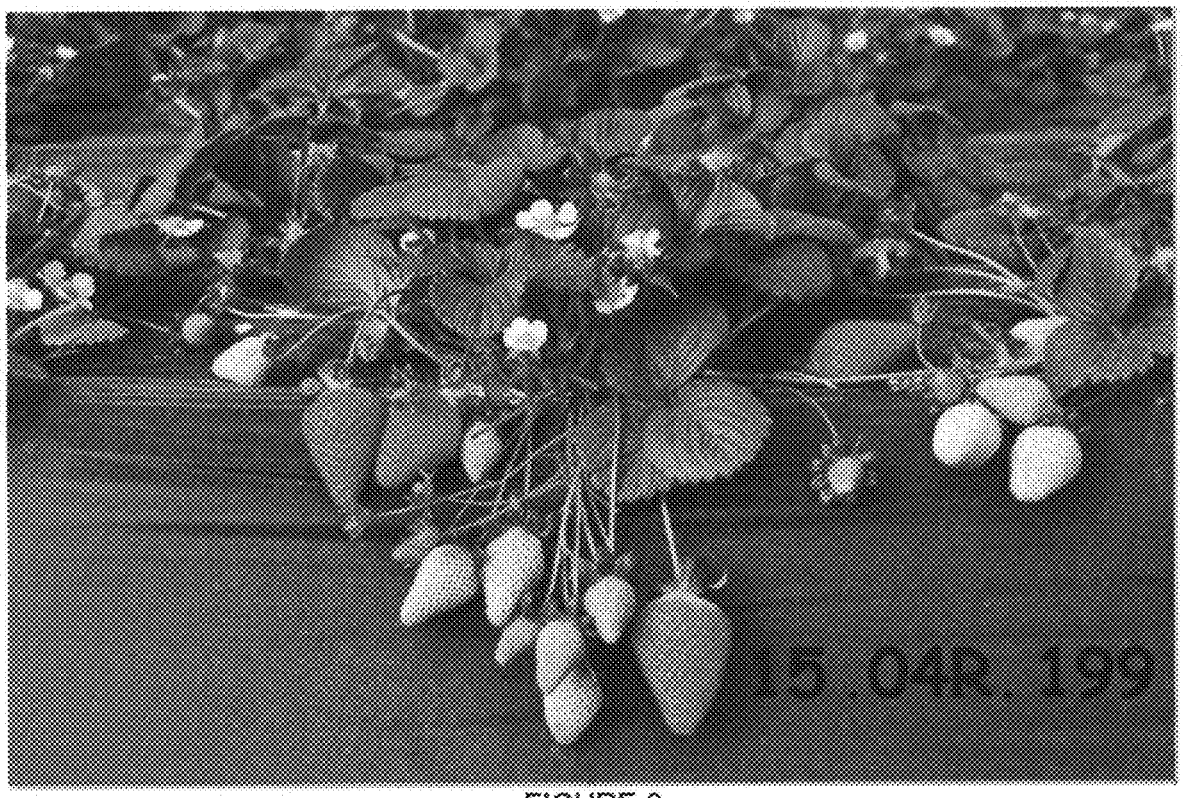
FIG. 2 shows several plants of the new variety which exhibit a semi-upright habit, a medium density plant and the position of the inflorescence at the same level as the foliage.
Figure 3:
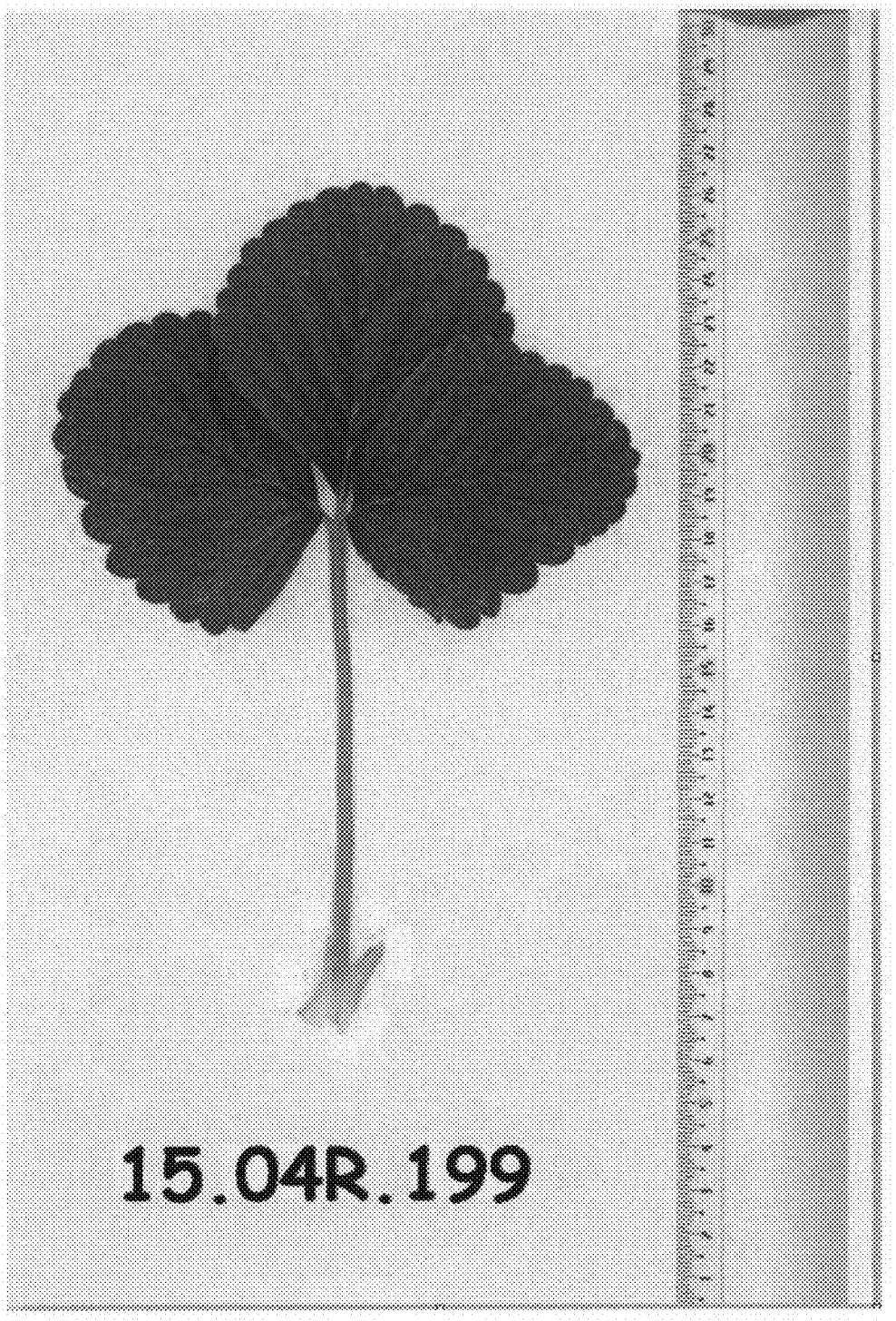
FIG. 3 shows the upper side of a complete leaf of the new variety. The leaf color of the upper side is RHS green near 141 B to 141 A.
Figure 4:
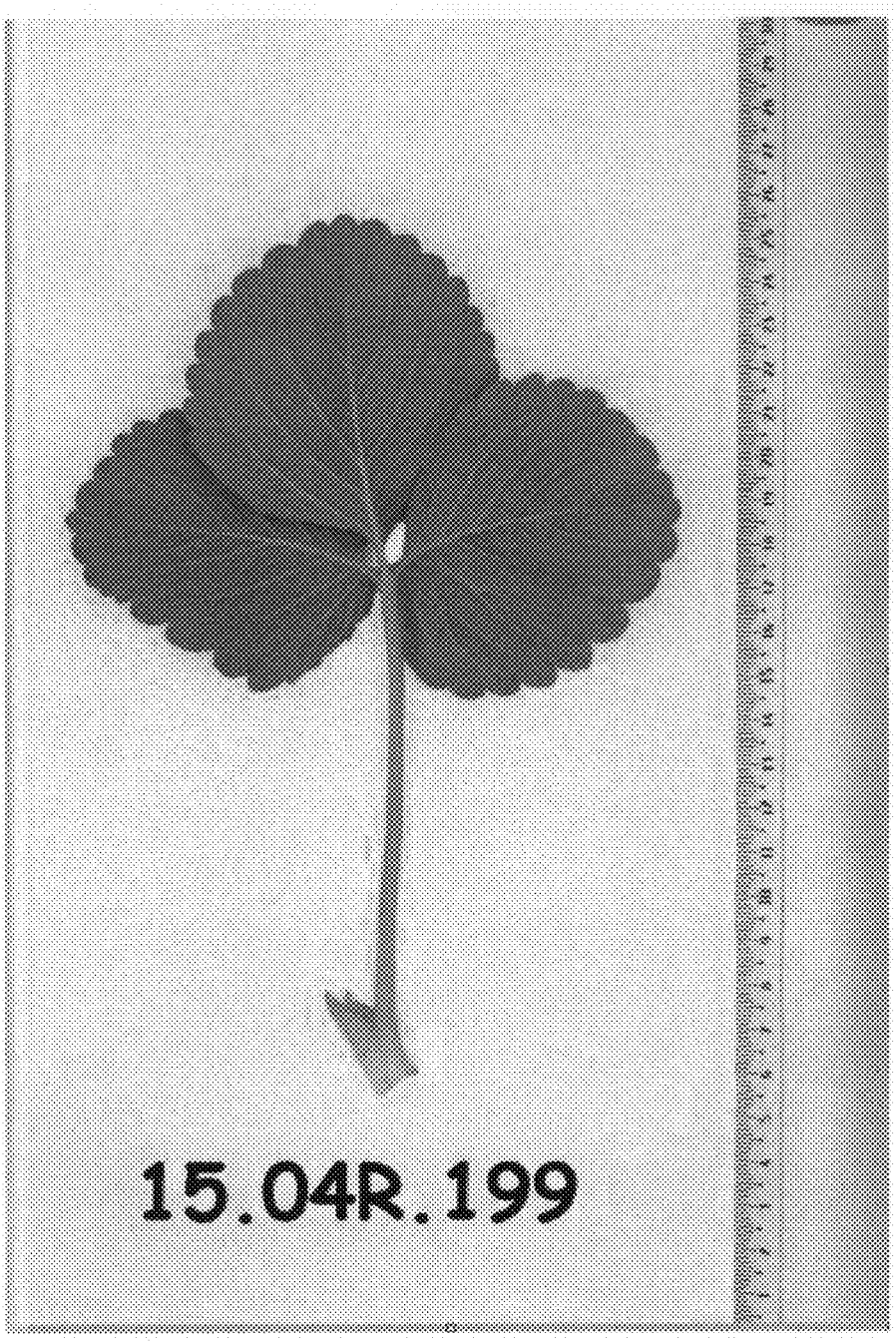
FIG. 4 shows the underside of a complete leaf of the new variety. The leaf color of underside is RHS Green near 143 B to 143 A.
Figure 5:
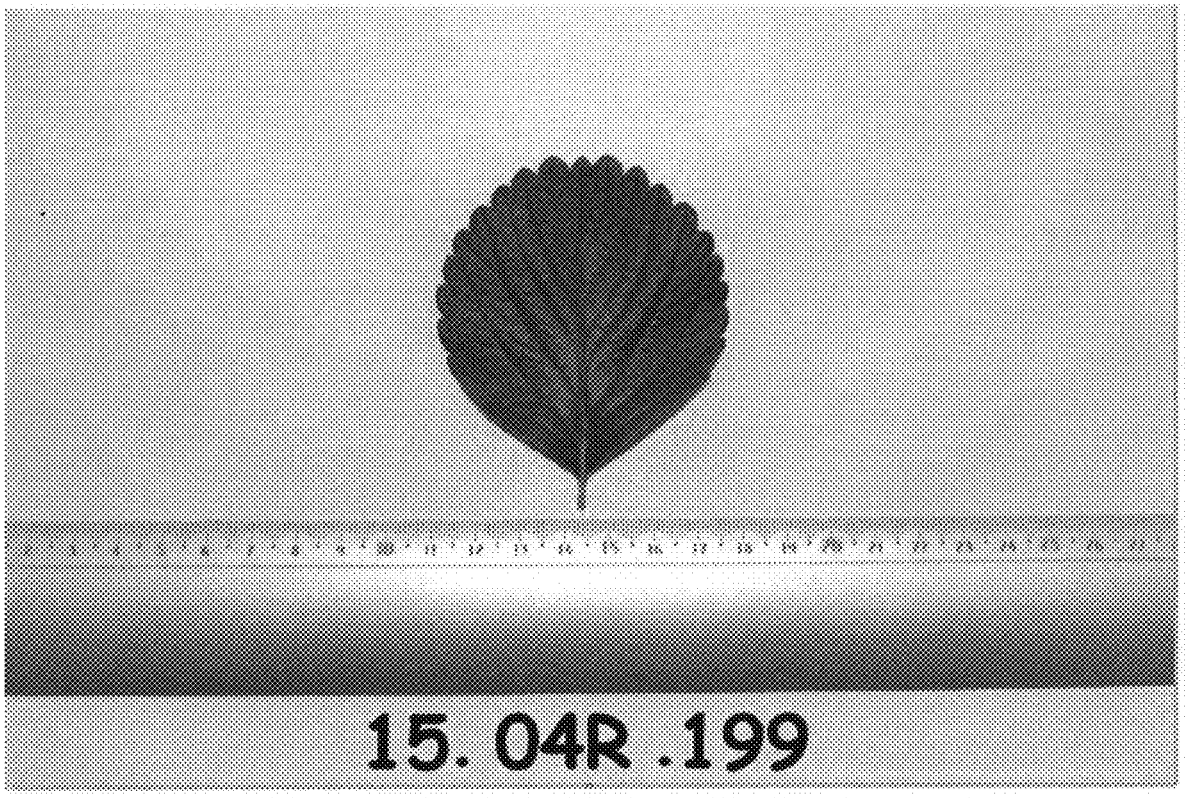
FIG. 5 and FIG. 6 show the upper side and the underside, respectively, of the terminal leaflet of the new variety. The obtuse shape of the base can be observed.
Figure 6:
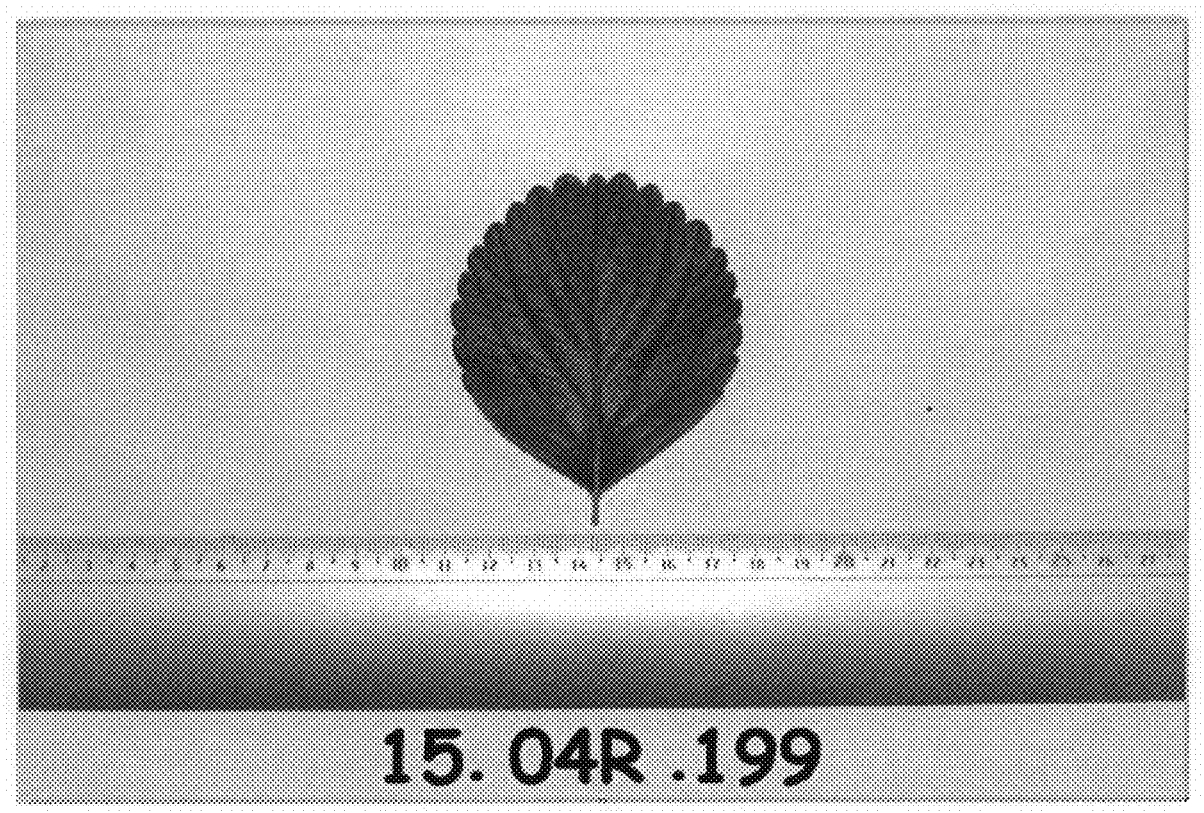
Figure 7:
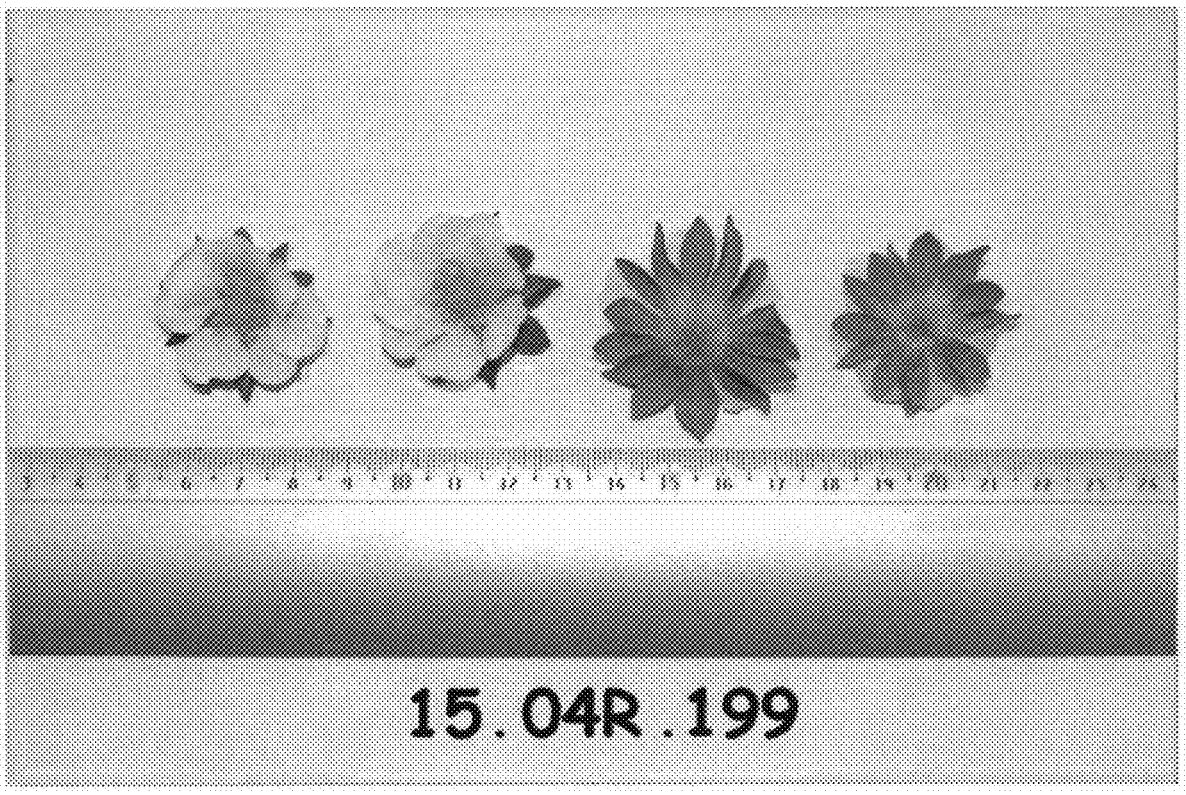
FIG. 7 shows several flowers of the new variety.
Figure 8:
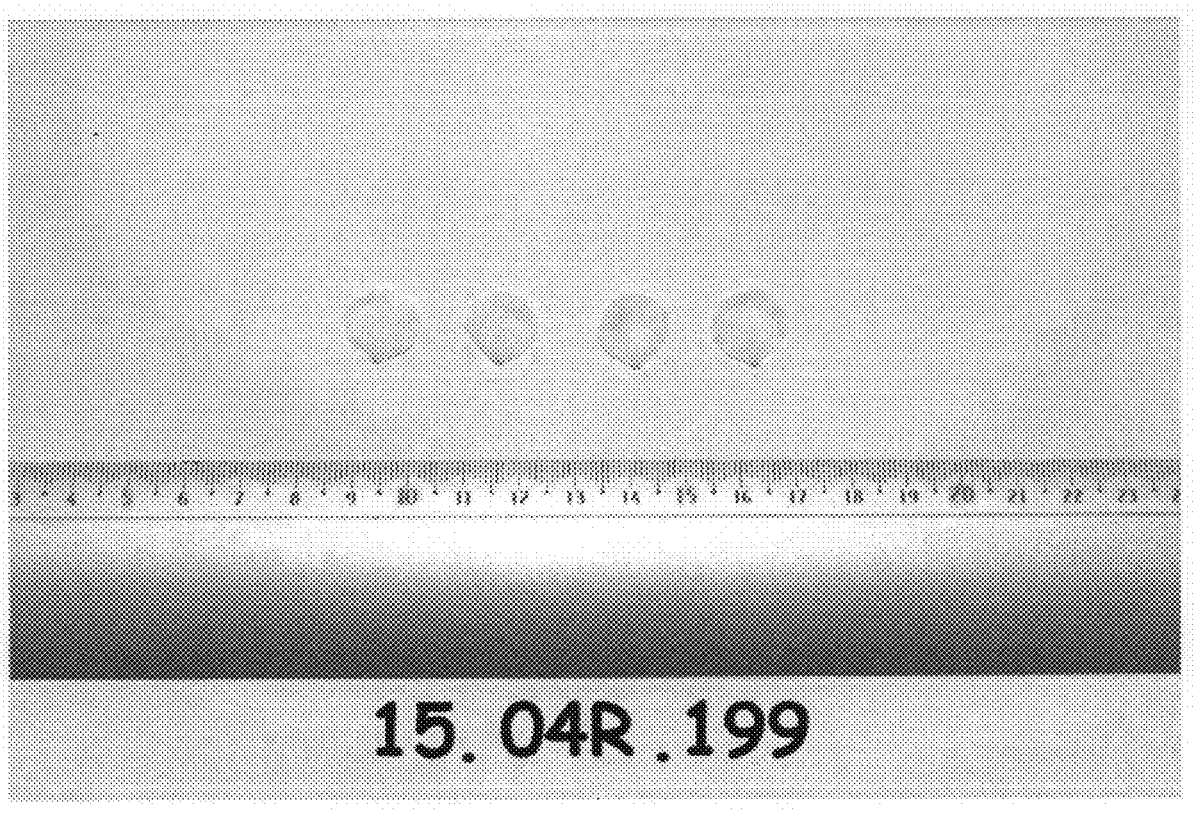
FIG. 8 shows several petals of the new variety: the upper side is represented by the two petals on the left, and the underside is represented by the two petals on the right.
Figure 9:
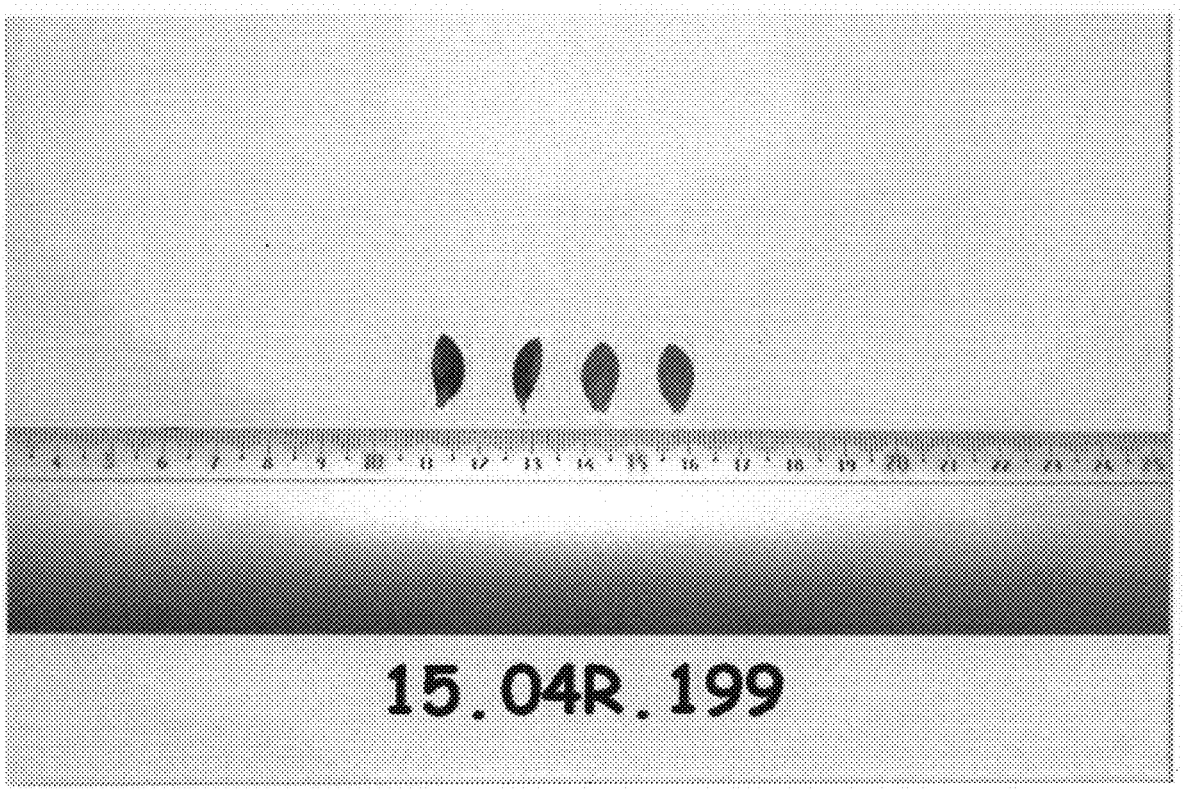
FIG. 9 shows the upper side and underside of typical sepals of the new variety. The upper side is represented by the two sepals on the left, RHS Green near 139 B to 139 A, and the underside is represented by the two sepals on the right, RHS Green near 143 B to 143 A.
Figure 10:
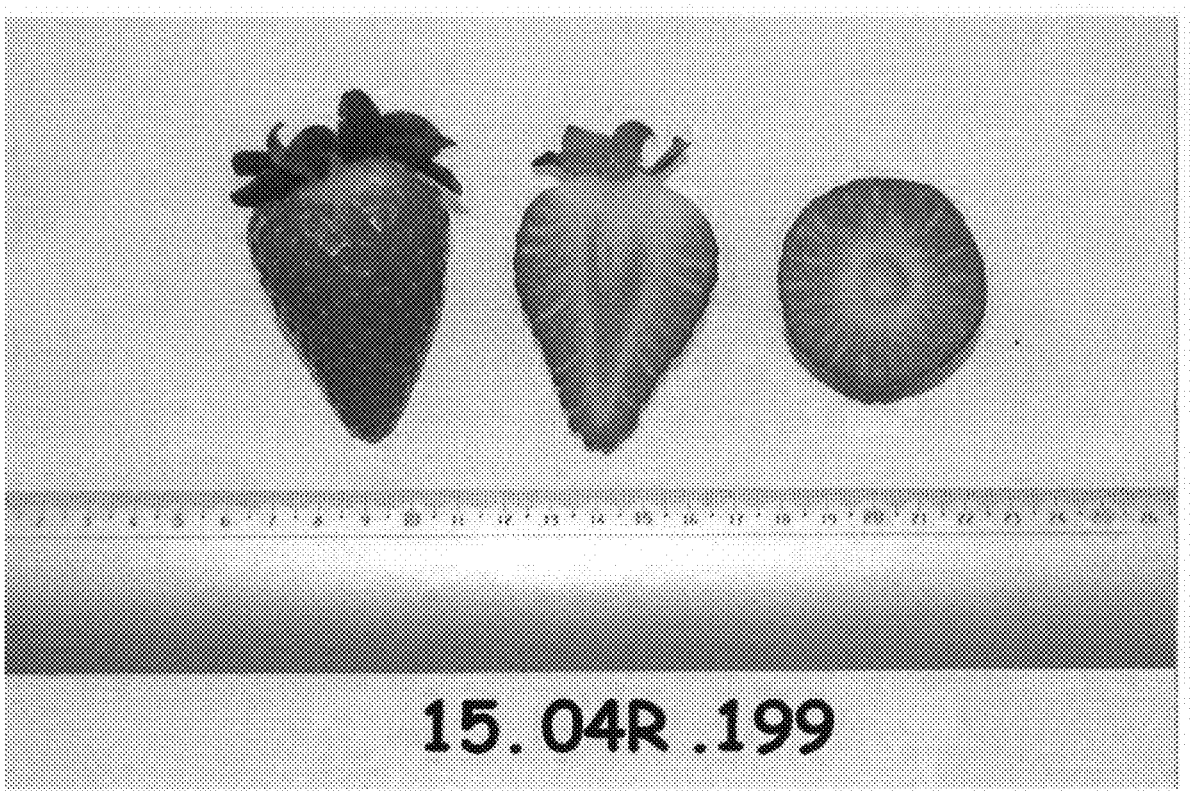
FIG. 10 shows typical fruit of the new variety whole, sliced and in cross section, illustrating the typical medium red fruit color (RHS Red near 44 A to 45 B), the typical orange red flesh coloration (RHS Orange-Red near 34 B to 34 A) lightening toward the center, with an absent or small hollow center.
Figure 11:
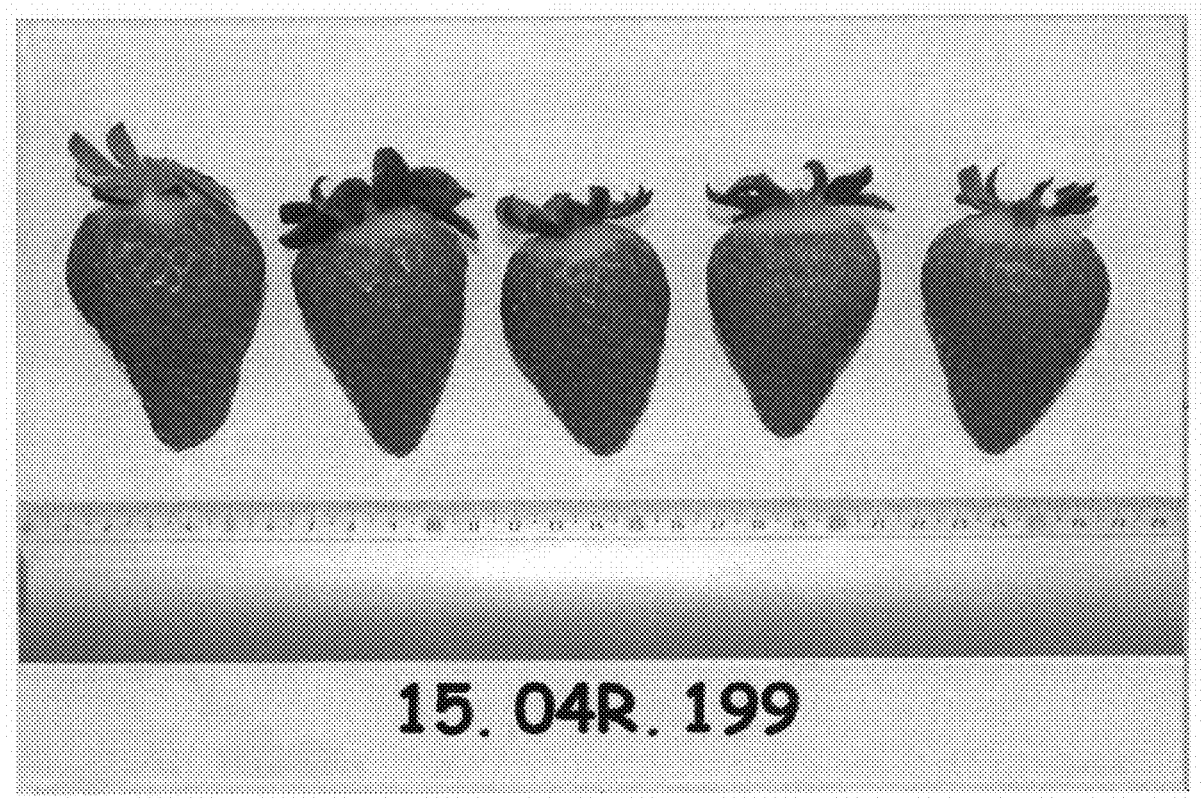
FIG. 11 shows several typical fruits of the new variety illustrating the typical conical shape and medium red fruit color (RHS Red near 44 A to 45 B).
Figure 12:
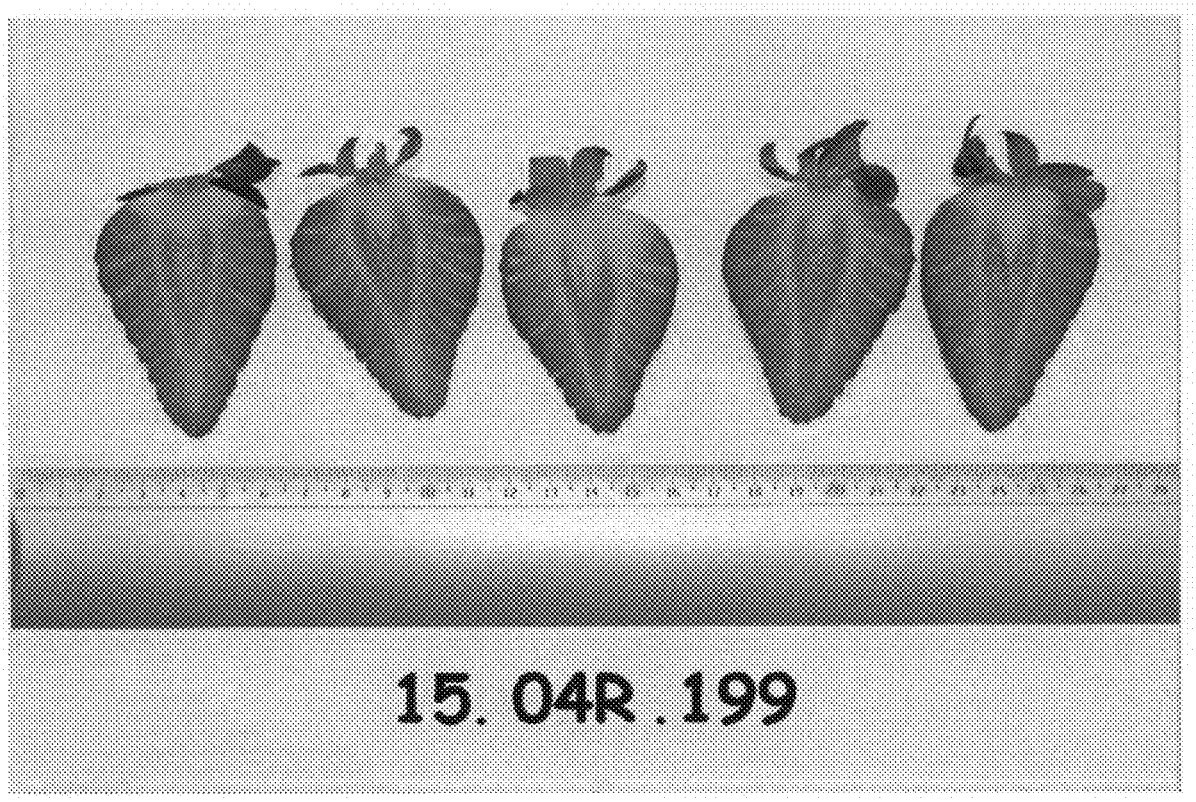
FIG. 12 shows several typical fruits of the new variety in cross section illustrating the typical orange red flesh coloration (RHS Orange-Red near 34 B to 34 A) lightening toward the center, with an absent or small hollow center.
Figure 13:
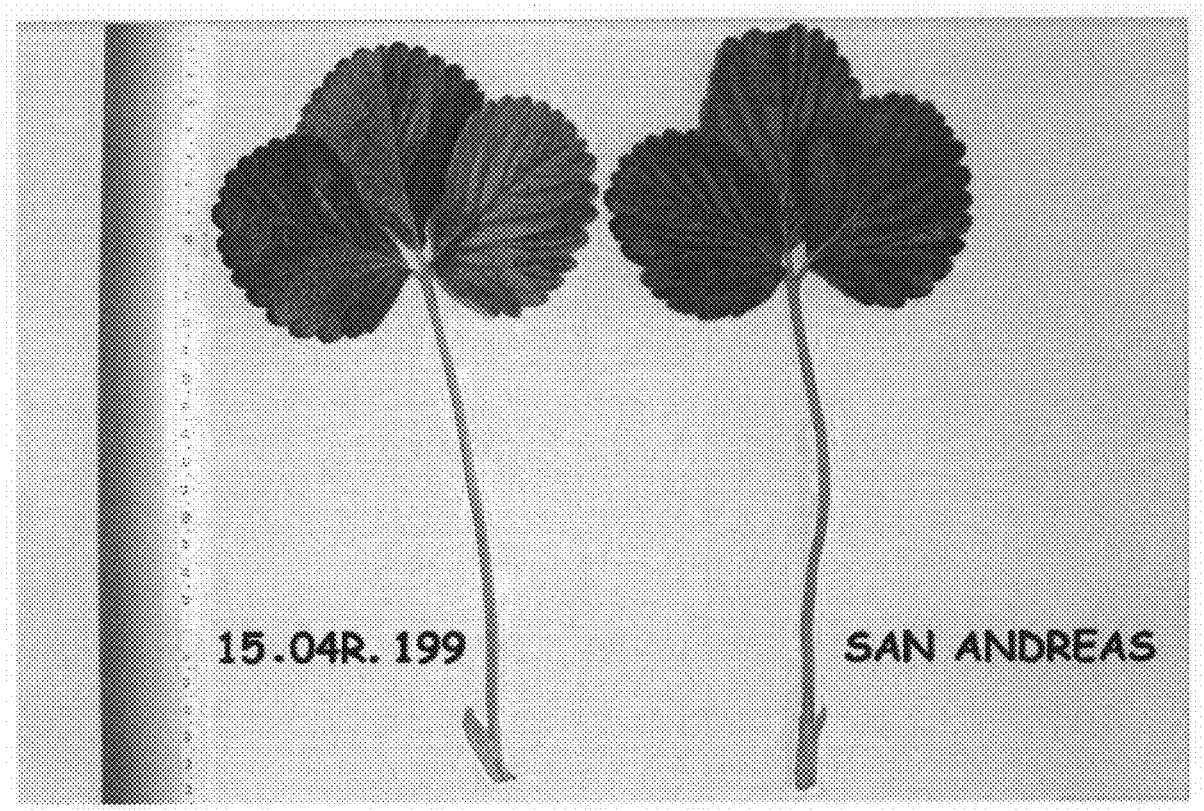
FIG. 13 shows the upper side of a complete leaf of the new variety with an RHS Green group color near 141 B to 141 A and a crenate terminal leaflet margin, in comparison with the upper side of a complete leaf of strawberry variety 'San Andreas', with an RHS Green group color near 135 B to 135 A and a serrate to crenate terminal leaflet margin.
Figure 14:
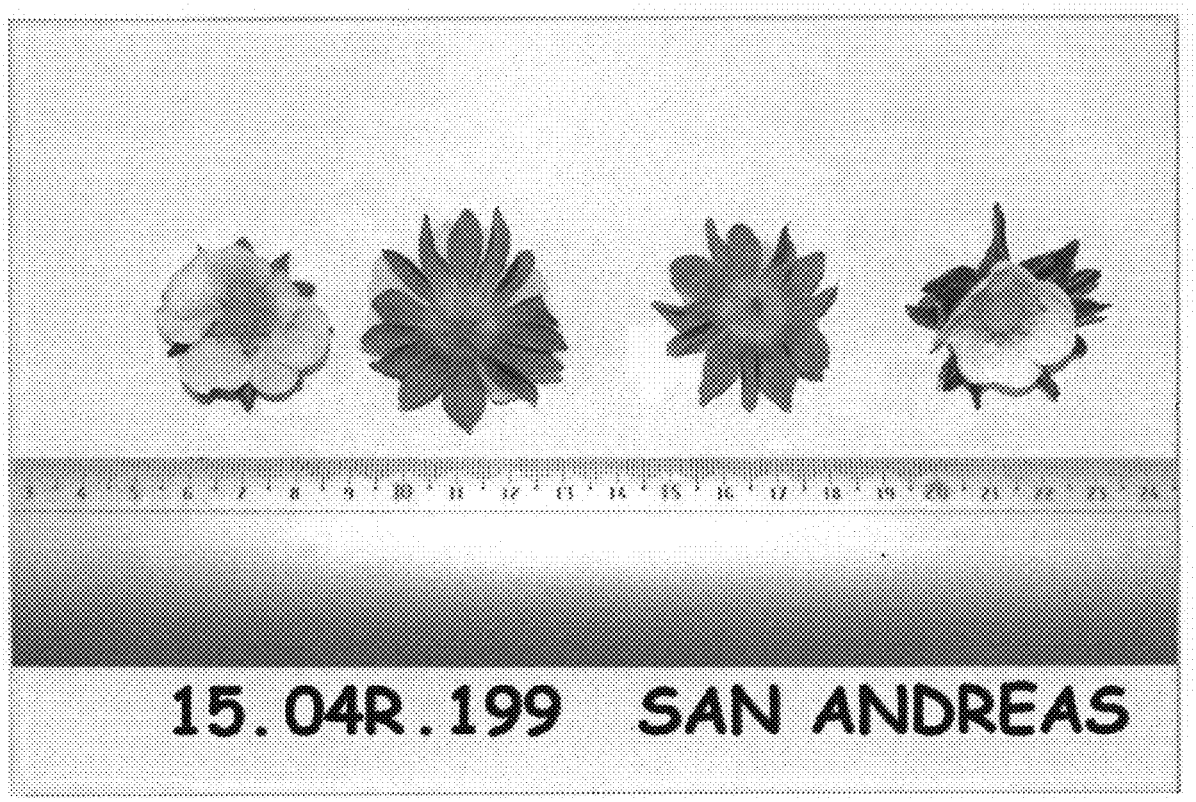
FIG. 14 shows a comparison between flowers of the new variety (designated 15.04R.199) and the strawberry variety 'San Andreas'. The flower of 'San Andreas' shows the same size the of calyx in relation to the corolla, whereas the flower of new variety shows a larger size calyx in relation to the corolla.
Figure 15:
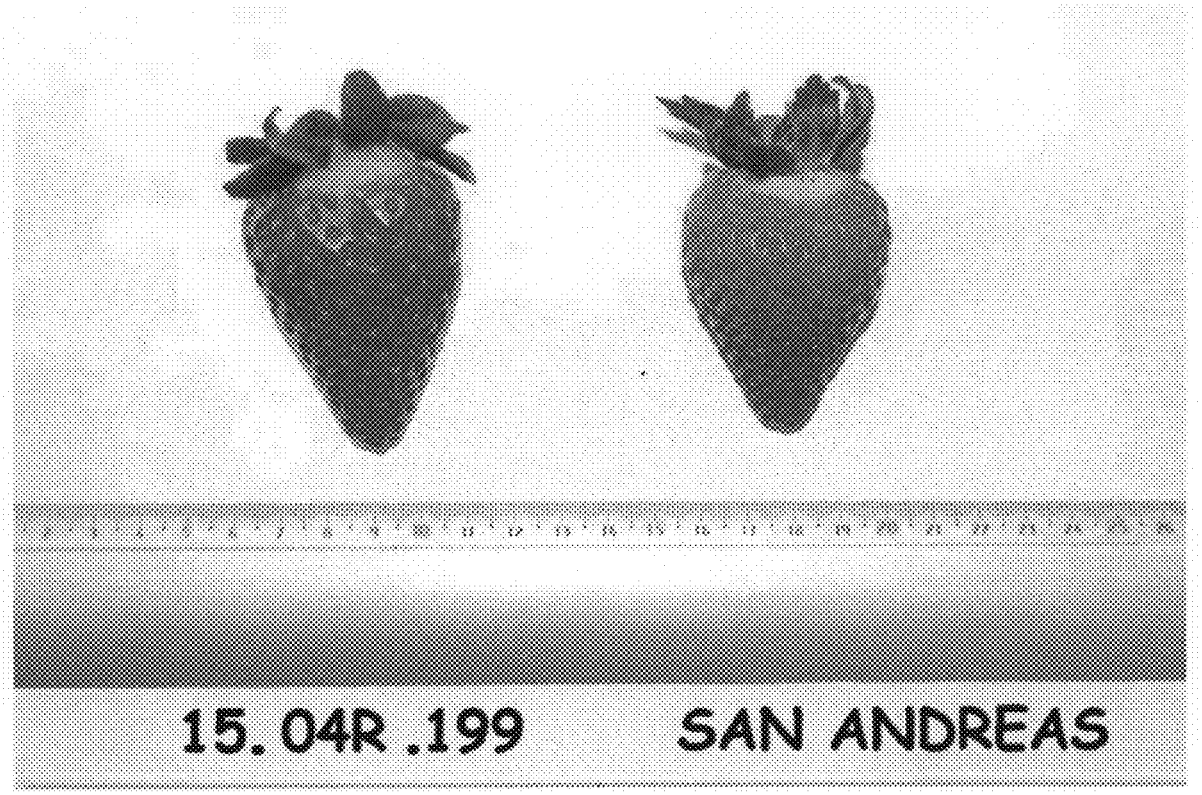
FIG. 15 shows a comparison between whole fruits of the new variety (designated 15.04R.199) and the strawberry variety 'San Andreas'. The fruit of 'San Andreas' has a medium fruit size, a narrow band without achenes and the sepals have an upward attitude, whereas the fruit of the new variety is larger, with a medium band without achenes and the attitude of the sepals is upwards to outwards.
Figure 16:
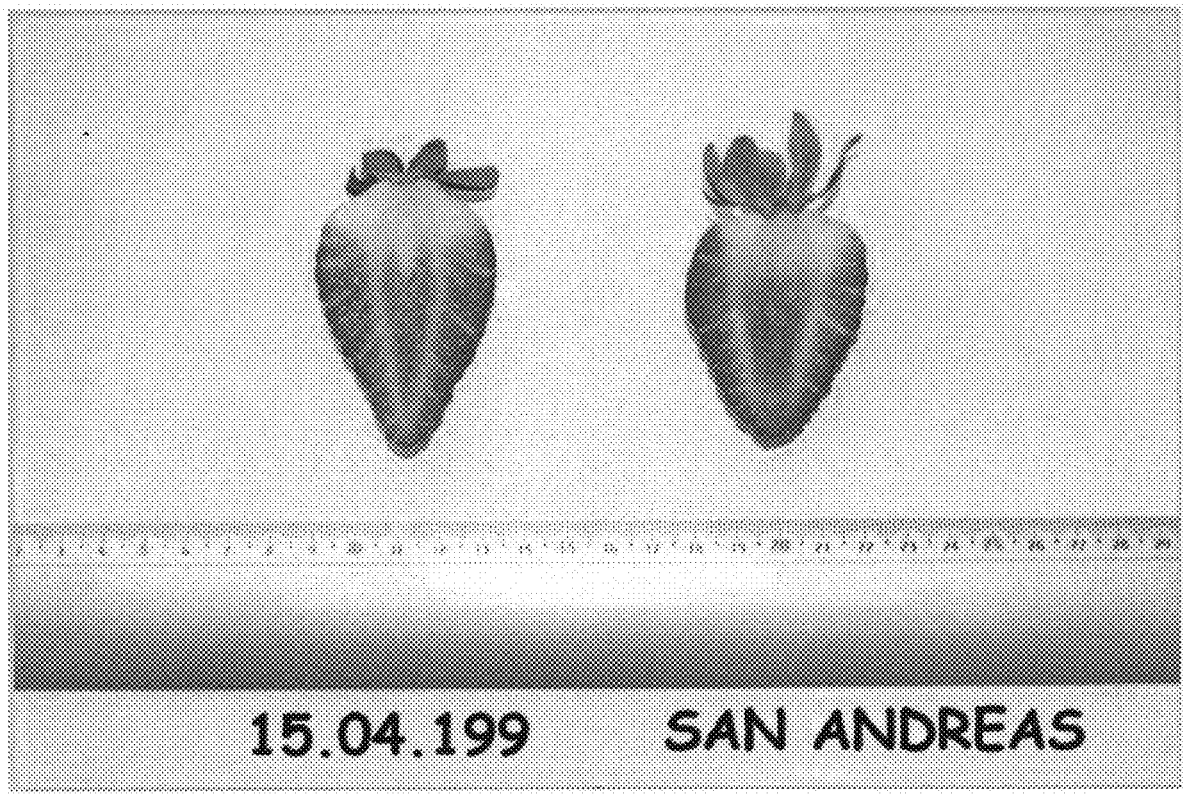
FIG. 16 shows a comparison of the fruit in cross section of the new variety (designated 15.04R.199) and the fruit in cross section of the strawberry variety 'San Andreas'. The position of the calyx attachment is level with the fruit for 'San Andreas', whereas in the fruit of the new variety the position of the calyx attachment is raised.

Throughout this specification, color names beginning with a small letter signify that the name of that color, as used in common speech is apply descriptive. Color names beginning with capital letter designate values based upon The R.H.S. Colour Chart published by The Royal Horticultural society, London, England, 1995. The color descriptions and other phenotypical descriptions may deviate from the stated values and descriptions depending upon variation in environmental, seasonal, climatic and cultural conditions.

The following detailed description of the new variety is based upon observations taken of plants and fruits grown under tunnel at the farm La Mogalla, in Cartaya (Huelva), Spain (7° W., 37° N., 45 feet elevation). Refrigerated plants were planted on August 4 (Summer Planted) to produce fruit in autumn and fresh plants were planted on September 24 (Fall Planted) to produce fruit during the spring of following year; with a sample size of two repetitions and 250 plants per repetition for each date of planting. After planting, plants were grown under tunnels in raised beds covered with plastic and with small holes in plastic walls. Water and fertilizer were applied trough drip irrigation.

The new variety is principally propagated by way of runners. Although propagation by runners is presently preferred, other known methods of propagating strawberry plants may be used. Strawberries root well after transplanting.

The term "blistering" used herein refers to the texture or rugosity or surface undulation inherent to leaves and is generally a constant characteristic.

'Plared 15105' is a fully remontant variety and self-fertile. It produces large quantities of pollen throughout the seasons and pollination is generally good as there are very few malformed fruit.

TABLE 1

Table 1 shows the Accumulated Summer planting production of Commercial Quality Fruit (g/plant) of the new variety 'Plared 15105' when compared to varieties 'San Andreas' (U.S. Plant Pat. No. 19,975) and 'Monterey' (U.S. Plant Pat. No. 19,767) during the months of October, November and December.

| Variety | 31-Octber | 30-November | 31-December |
|---|---|---|---|
| Plared 15105 | 100 | 214 | 352 |
| San Andreas | 42 | 159 | 276 |
| Monterey | 78 | 96 | 212 |

TABLE 2

Table 2 shows the Accumulated Fall planting production of Commercial Quality Fruit (g/plant) of the new variety 'Plared 15105' when compared to varieties 'San Andreas' and 'Monterey' during the months of March, April and May.

| Variety | 1-March | 31-March | 30-April | 20-May |
|---|---|---|---|---|
| Plared 15105 | 419 | 706 | 927 | 1242 |
| San Andreas | 190 | 404 | 700 | 917 |
| Monterey | 120 | 449 | 867 | 1109 |

TABLE 3

Table 3 shows the Total Yield (g/plant) of Summer plantings from October 7 and fruit weight average of the new variety 'Plared 15105' when compared to varieties 'San Andreas' and 'Monterey' to December 31.

| Variety | $1^{st}$ + $2^{nd}$ Quality Fruit | Total | Weight (g/fruit) |
|---|---|---|---|
| Plared 15105 | 100 | 214 | 352 |
| San Andreas | 42 | 159 | 276 |
| Monterey | 78 | 96 | 212 |

TABLE 4

Table 4 shows the Total Yield (g/plant) of Fall plantings from January 2 and the fruit weight average of the new variety 'Plared 15105' when compared to \ varieties 'San Andreas' and 'Monterey' to May 20.

| Variety | $1^{st}$ + $2^{nd}$ Quality Fruit | Total | Weight (g/fruit) |
|---|---|---|---|
| Plared 15105 | 1242 + 198 | 1440 | 27-24 |
| San Andreas | 917 + 366 | 1283 | 25-21 |
| Monterey | 1109 + 191 | 1300 | 24-22 |

TABLE 5

TABLE 5 shows the Production Total of Summer plantings, to December 31 of First Quality Fruit ($1^{st}$ quality) and Second Quality Fruit ($2^{nd}$ quality) in g/plant, of the new variety 'Plared 15105' when compared to varieties 'San Andreas' and 'Monterey'.

| Variety | $1^{st}$ quality | $2^{nd}$ quality | TOTAL ($1^{st}$ quality + $2^{nd}$ Quality) | $2^{nd}$ quality |
|---|---|---|---|---|
| Plared 15105 | 352 | 108 | 460 | 23.5 |
| San Andreas | 212 | 57 | 269 | 21.2 |
| Monterey | 276 | 72 | 348 | 20.7 |

$$\% \ 2^{nd} \text{ quality} = \frac{2^{nd} \text{ quality}}{\text{TOTAL}} \times 100$$

TABLE 6

TABLE 6 shows the Production Total of Fall plantings, to May 20 of First Quality Fruit ($1^{st}$ quality) and Second Quality Fruit ($2^{nd}$ quality) in g/plant, of the new variety 'Plared 15105' when compared to varieties 'San Andreas' and 'Monterey'.

| Variety | $1^{st}$ quality | $2^{nd}$ quality | TOTAL ($1^{st}$ quality + $2^{nd}$ quality) | $2^{nd}$ quality |
|---|---|---|---|---|
| Plared 15105 | 1242 | 198 | 1440 | 13.7 |
| San Andreas | 917 | 366 | 1283 | 28.5 |

$$\% \ 2^{nd} \text{ quality} = \frac{2^{nd} \text{ quality}}{\text{TOTAL}} \times 100$$

TABLE 7

Table 7 shows the Summer planting Weight (g/Fruit) at two dates: October 31 and December 31 of the new variety 'Plared 15105' when compared to varieties 'San Andreas' and 'Monterey'.

| WEIGHT (g/fruit) | October 31 | December 31 |
|---|---|---|
| Plared 1505 | 24 | 23 |
| San Andreas | 23 | 22 |
| Monterey | 22 | 21 |

WEIGHT is shown as the average weight per fruit in First Quality Fruits.

TABLE 8

Table 8 shows the Fall planting Weight (g/Fruit) at two dates: Mars 1 and May 18 of the new variety 'Plared 15105' when compared to varieties 'San Andreas' and 'Monterey'.

| WEIGHT (g/fruit) | Mars 1 | May 20 |
|---|---|---|
| Plared 1505 | 27 | 24 |
| San Andreas | 25 | 21 |
| Monterey | 24 | 22 |

WEIGHT is shown as the average weight per fruit in First Quality Fruits.

TABLE 9

Table 9 shows a comparison of the fruit analysis between the new variety 'Plared 15105' and varieties 'San Andreas' and 'Monterey'.

FRUIT ANALYSIS

| | San Andreas | Plared 15105 (15.04R.199) | Monterey |
|---|---|---|---|
| Firmness (Kg) | 0.90 | 0.80 | 0.80 |
| Humidity & Volatile Matter (%) | 92.10 | 93.60 | 93.10 |
| Dry Matter (%) | 7.90 | 6.40 | 6.90 |
| PH (to 20°) | 3.40 | 3.40 | 3.40 |
| Acidity as Anhydride Citric (%) | 0.82 | 0.70 | 0.76 |
| Soluble Solids (°Brix) | 8.00 | 6.40 | 6.70 |
| Maturity Index | 9.80 | 9.40 | 8.80 |
| Content in Ascorbic Acid (ppm) | 22.30 | 24.10 | 19.60 |
| Dominant Tonality (nm) | 505 | 500 | 500 |
| Luminosity: | | | |
| Transmitance to 460 nm | 17.40 | 19.30 | 21.70 |

The following definitions apply:

Firmness is the fruit's resistance to penetration measured in Kilograms (Kg). The measures given were obtained by a penetrometer ROZE Mod. Arbelette, with a 50 mm2 section head.

Dry Matter is the weight of the residual left from the trituration of the fruit after the drying process at a temperature of 103° C.+2° C. until reaching constant weight.

$$(\%)\ \text{Dry Matter} = \frac{\text{Weight dry matter} \times 100}{\text{Weight Fresh Matter}}$$

Humidity & Volatile Matter represents the content in volatile matters and water of the fruits.

$$(\%)\ \text{Humidity \& Volatile Matter} = 100 - \%\ \text{Dry Matter}$$

Maturity Index is the Relation between Soluble solids and Acidity as Anhydride Citric.

$$\text{Maturity Index} = \frac{\text{Soluble solids}}{\text{Acidity as Anhydride Citric}}$$

DETAILED DESCRIPTION OF THE NEW VARIETY

The following additional information is provided to further describe the new variety.

Plant:

*Habit*.—Semi-upright.
*Density*.—Medium.
*Vigor*.—Medium.
*Height*.—Medium, about 24 cm.
*Width*.—Medium, about 21 cm.

Leaf:

*Upperside color*.—About RHS Green group color near 141 B to 141 A.
*Underside color*.—About RHS Green group color near 143 B to 143 A.
*Length*.—Approximately 18.5 cm to 19.5 cm.
*Width*.—Approximately 13 cm to 14 cm.
*Shape in cross section*.—Concave.
*Leaf surface undulation or blistering*.—Medium.
*Number of leaflets*.—Three only.
*Variegation*.—Absent.
*Glossiness*.—Weak.

Leaf stem characteristics:

*Color*.—About RHS Yellow-Green group near 144 B to 144 A.
*Position of hairs*.—Slightly outwards.
*Length*.—Long, approximately21.5 cm to 22.5 cm.

Terminal leaflet:

*Upperside color*.—About RHS Green group color near 141 B to 141 A.
*Underside color*.—About RHS Green group color near 143 B to 143 A.
*Length/width ratio*.—Moderately longer.
*Length*.—Long, approximately 7.5 cm to 8.0 cm.
*Width*.—Medium, approximately 6.0 cm to 6.5 cm.
*Shape in cross section*.—Concave.
*Shape of base*.—Obtuse.
*Margin*.—Crenate.
*Apex shape*.—Rounded.

Petiole:

*Attitude of hairs*.—Horizontal.
*Color*.—About RHS Yellow-Green group near 144 B to 144 A.
*Length*.—Long, about 21.5 cm to 22.5 cm.

Stipule:

*Anthocyanin coloration*.—Absent or very weakly expressed, RHS Yellow-Green group coloration near 145 C to 145 B.
*Length*.—Short, approximately 2.0 cm to 2.5 cm.

Stolons:

*Number*.—Medium, about 8.
*Length*.—Medium, approximately 28 cm to 33 cm.
*Thickness*.—Medium, approximately 3.5 mm to 4.0 mm.
*Pubescence density*.—Medium.
*Color*.—About RHS Yellow-Green group near 144 B to 144 A.
*Anthocyanin coloration*.—Absent.

Inflorescence:
*Position relative to foliage*.—Same level.
*Number of flowers*.—Medium, about 6 to 8.
Pedicel:
*Position of hairs*.—Slightly outwards.
*Average length*.—Approximately 16.5 to 17.5 cm.
*Average diameter*.—Approximately 2.9 to 3.5 mm.
*Color*.—About RHS Yellow-Green group near 145 B to 145 A.
Flower:
*Size*.—Medium.
*Size of calyx relative to corolla*.—Larger.
*Arrangement of petals*.—Overlapping.
*Diameter primary flowers*.—Long, approximately 3.2 cm to 3.6 cm.
*Diameter secondary flowers*.—Medium, approximately 2.9 cm to 3.2 cm.
*Number of petals*.—About 7-8.
*Fragrance*.—No significant fragrance.
*Fall planted*.—Time from bloom to mature fruit (in Huelva, Spain): About 18 to 20 days.
*Summer planted time from bloom to mature fruit* (*in Huelva, Spain*).—About 27 to 29 days.
*Stamens*.—Present and numerous with pollen present, fertile and abundant. Length: Approximately 3.8 mm to 3.9 mm. Color: About RHS Green-White group (near 157D to 157 C).
*Anthers*.—Generally average in size.
*Color*.—About RHS Yellow group near 13 C to 13 B and darkening with advanced maturity.
*Pollen*.—Fertile and abundant. Color: About RHS Yellow-Orange group near 16 C to 16 B.
*Pistils*.—Abundant. Size: Medium. Color: About RHS Yellow group near 13 C to 14 C.
Petal:
*Length/width ratio*.—Equal.
*Length*.—Long, approximately 8 mm to 9 mm.
*Width*.—Long, approximately 9 mm to 10 mm.
*Shape*.—Rounded.
*Color*.—RHS White group (near 155 C to 155 B).
*Shape of base*.—Obtuse and get narrower.
*Shape of apex*.—Rounded.
*Petal margin*.—Glabrous.
Sepal:
*Calyx*.—Presents 12 to 13 sepals with lanceolate shape.
*Attitude of sepals*.—Upwards to outwards.
*Color upperside of sepals*.—About RHS Green group near 139 B to 139 A.
*Color underside of sepals*.—About RHS Green group near 143 B to 143 A.
*Length of sepals*.—Long, approximately 12 mm to 14 mm.
*Width of sepals*.—Long, approximately 5 mm to 7 mm.
*Margin type of sepal*.—Smooth.
*Apex shape*.—Ovate, slightly acuminate.
*Base shape*.—Straight to get narrower.
Fruit:
*Ratio of length/maximum width*.—Moderately longer.
*Color*.—About RHS Red group near 44 A to 45 B.
*Peduncle length of inflorescence stem primary fruit*.—About 20 cm to 22 cm.
*Peduncle length of inflorescence stem of secondary fruit*.—About 15 cm to 18 cm.
*Peduncle of inflorescence stem color*.—About RHS Yellow-Green group near 145 B to 145 A.
*Length primary fruit*.—Long, approximately 5.5 cm to 6.4 cm.
*Width primary fruit*.—Medium, approximately 4.1 cm to 4.6 cm.
*Length secondary fruit*.—Long, approximately 4.9 cm to 5.3 cm.
*Width secondary fruit*.—Medium, approximately 3.4 cm to 3.9 cm.
*Size*.—Large.
*Shape*.—Conical.
*Difference in shapes between primary and secondary fruits*.—Slight.
*Band without achenes*.—Medium.
*Color of achenes*.—About RHS Orange to Red group near 42 D to 42 C.
*Evenness of surface*.—Slightly uneven.
*Evenness of color*.—Even or very slightly uneven.
*Glossiness*.—Medium.
*Position of achenes*.—Below surface.
*Insertion of calyx*.—Raised.
*Size of calyx in relation to fruit diameter*.—Same size.
*Adherence of calyx*.—Strong.
*Firmness*.—Firm.
*Color of flesh*.—About RHS Orange-Red group near 34 B to 34 A, lightening toward center.
*Distribution of orange red color of flesh*.—Marginal.
*Hollow center*.—Absent or small.
*Color of core*.—About RHS Orange-Red group near 32 B to 32 A.
*Sweetness*.—Medium, approximately 6.40° Brix.
*Acidity*.—Medium, approximately 0.70%.
*Time of flowering* (50% *of plants at first flower*).—Very early.
*Time of ripening* (50% *of plants with ripe fruits*).—Very early.
*Type of bearing*.—Fully remontant.
Fruiting truss:
*Attitude*.—Semi-erect.
General:
Summer plantation:
*Planting date*.—August 4.
10% *flowering*.—September 1.
*First mature fruits*.—September 25.
*Maturity* (15-20 *g/plant*).—October 10.
Date of planting: August 4 in the farm of La Mogalla, in Cartaya (Huelva), Spain, about 7° W, 37° N, 45 feet elevation.
Time of flowering: 10% flowering occurs about September 1 with first mature fruit about September 25 and maturity (15-20 g/plant) about October 10.
Time of flowers (50% of plants at first flower): about September 10.
Fall plantation:
*Planting date*.—September 24.
10% *flowering*.—October 15.
*First mature fruits*.—November 15.
*Maturity* (15-20 *g/plant*).—December 5.
Date of planting: Sep. 24, 2018 in the farm of La Mogalla, in Cartaya (Huelva), Spain, about 7° W, 37° N, 45 feet elevation.
Time of flowering: 10% flowering occurs about October 15 with first mature fruit about November 15 and maturity (15-20 g/plant) about December 5.
Time of flowers (50% of plants at first flower): About October 28.

Storage qualities:

Shipping quality: Fruits of 'Plared 15105' maintain their quality characteristics for 60 hours when shipped under refrigeration at a temperature of about 2° C.

Fruit storage life of 'Plared 15105' is medium: 6 to 8 days at temperatures of about 4 to 5° Centigrade.

Fruit market use: Fruits of 'Plared 15105' are suitable for consumption as fresh fruit. Also, they are suitable for processing.

Summer plantation:

Time of ripening: After planting as aforesaid, plants are grown in raised beds covered with plastic and with small holes in plastic walls, creating a tunnel. Water and fertilizer are applied through drip irrigation. Time of ripening (50% of plants with ripe fruit) is about October 1. The first mature fruit is about September 25 and maturity (15-20 g/plant) is about October 10.

Fall plantation:

Time of ripening: After planting as aforesaid, plants are grown in raised beds covered with plastic and with small holes in the plastic walls, creating a tunnel. Water and fertilizer are applied through drip irrigation. Time of ripening (50% of plants with ripe fruit) is about November 26. The first mature fruit is about November 15 and maturity (15-20 g/plant) is about December 5.

disease resistance: No particular sensitivity to any disease or parasite has been observed for 'Plared 15105'.

I claim:

1. A new and distinct strawberry variety substantially as shown and described.

* * * * *